United States Patent [19]
Fujiwara et al.

[11] Patent Number: 6,071,866
[45] Date of Patent: *Jun. 6, 2000

[54] MILD ANTIMICROBIAL LIQUID CLEANSING FORMULATIONS COMPRISING HYDROXY ACID BUFFERING COMPOUND OR COMPOUNDS AS POTENTIATOR OF ANTIMICROBIAL EFFECTIVENESS

[75] Inventors: Mitsuko Fujiwara, Urbana, Ill.; Carol Kregler Vincent, Wanaque, N.J.; Kavssery Ananthapadmanabhan, New Windsor, N.Y.; Virgilio Villa, Bergenfield, N.J.

[73] Assignee: Lever Brothers Company, Division of Conopco, Inc., New York, N.Y.

[ * ] Notice: This patent is subject to a terminal disclaimer.

[21] Appl. No.: 09/205,984

[22] Filed: Dec. 4, 1998

Related U.S. Application Data

[63] Continuation-in-part of application No. 08/810,114, Feb. 25, 1997, Pat. No. 5,914,300, which is a continuation-in-part of application No. 08/252,298, Jun. 1, 1994, Pat. No. 5,681,802.

[51] Int. Cl.[7] ............................. C11D 1/94; C11D 3/20; C11D 3/48
[52] U.S. Cl. .................. 510/130; 510/131; 510/159; 510/382; 510/383; 510/387; 510/388; 510/405; 510/428; 510/488; 510/504
[58] Field of Search .................... 510/130, 131, 510/159, 382, 383, 387, 405, 388, 428, 488, 504

[56] References Cited

U.S. PATENT DOCUMENTS

| | | | |
|---|---|---|---|
| 4,100,097 | 7/1978 | O'Roark | 510/151 |
| 4,564,520 | 1/1986 | Ehrl et al. | 424/70 |
| 4,752,467 | 6/1988 | Konrad et al. | 424/70 |
| 4,839,080 | 6/1989 | Jungermann et al. | 510/131 |
| 5,002,680 | 3/1991 | Schmidt et al. | 252/90 |
| 5,132,037 | 7/1992 | Greene et al. | 252/108 |
| 5,137,715 | 8/1992 | Hoshowski et al. | 424/70 |
| 5,225,097 | 7/1993 | Kacher et al. | 252/112 |
| 5,227,086 | 7/1993 | Kacher et al. | 510/146 |
| 5,378,731 | 1/1995 | Andrews et al. | 514/552 |
| 5,409,640 | 4/1995 | Giret et al. | 510/417 |
| 5,429,815 | 7/1995 | Faryniarz et al. | 424/47 |
| 5,686,088 | 11/1997 | Mitra et al. | 424/404 |

FOREIGN PATENT DOCUMENTS

| | | |
|---|---|---|
| 0799612 | 10/1997 | European Pat. Off. . |
| 2301237 | 9/1976 | France . |
| 9117237 | 11/1991 | WIPO . |
| 9418292 | 8/1994 | WIPO . |

OTHER PUBLICATIONS

"Circulate 2513" from Ciba Geigy, 1990.

*Primary Examiner*—Lorna M. Douyon
*Attorney, Agent, or Firm*—Ronald A. Koatz

[57] ABSTRACT

Liquid skin cleansing compositions comprising (1) mild surfactant systems; (2) 0.5% to 9% by wt. of a hydroxy carboxylic compound or compounds which buffer the pH of the composition; (3) an antibacterial agent and (4) 1% to 99% water to potentiate the bactericidal activity are provided.

2 Claims, 1 Drawing Sheet

MILD ANTIMICROBIAL LIQUID CLEANSING FORMULATIONS COMPRISING HYDROXY ACID BUFFERING COMPOUND OR COMPOUNDS AS POTENTIATOR OF ANTIMICROBIAL EFFECTIVENESS

RELATED APPLICATIONS

This is a Continuation-in-Part of Ser. No. 08/810,114 filed Feb. 25, 1997, now U.S. Pat. No. 5,914,300 which in turn is a Continuation-in-Part of 08/252,298, filed Jun. 1, 1994 now U.S. Pat. No. 5,681,802.

BACKGROUND OF THE INVENTION

The present invention relates to one-phase liquid cleansing compositions having enhanced antimicrobial effectiveness. More specifically, the invention relates to a hydroxy acid compound or compounds, more particularly lactic acid which potentiate the antibacterial activity of liquid cleaning formulations by buffering the pH of the formulation such that the pH will rise no higher than 5.0, preferably between 2.5 to 5.0 under in use conditions (as opposed to initial pH).

There is a large demand in the market for mild liquid cleansing formulations which additionally have an antibacterial effect. Antibacterial cleansers are preferred because they kill germs and mild personal cleansers are preferred to minimize skin irritation, dryness, etc. However, the combination of mild cleansing formulations and strong antibacterial effect is difficult to achieve. Thus, for example, while soaps provide antibacterial effects, they are not mild to the skin. When very mild non-soap surfactants are used, antibacterial effect is greatly compromised.

The balancing act between providing mildness and effective antibacterial effectiveness is recognized for example in International Publication WO 92/18100. In this publication, improved clinical mildness is said to be provided through the use of a water soluble cationic polymer (see page 10, lines 24–29). Cationic polymer is apparently used instead of additional ethoxylated surfactant because the percent of ethoxylated mildness surfactant must be minimized in order not to affect antibacterial effectiveness (page 7, lines 4–6).

Another approach to providing mildness effect without affecting antibacterial properties is that which appears to be used by Dial in, for example, Liquid Dial Plus with Moisturizers Antibacterial Soap®. Here, mildness benefits are apparently provided by the use of moisturizing compounds rather than by the use of very mild surfactants alone (which, as indicated above, compromises antibacterial effectiveness).

In both cases, it can be readily seen that it is extremely difficult to provide effective antibacterial action in the presence of very mild surfactants, to use larger amounts of harsher surfactants or soaps and to mask the effects of the harshness by providing cationic mildness conditioning agents (WO 92/18100) or moisturizers (as in the Dial product).

It would be greatly beneficial if antibacterial effectiveness could be provided either by providing a compound or compounds which alone or together buffer pH of a liquid composition at a pH low enough to provide antibacterial effectiveness for that composition formulation (while maintaining stability of composition); or by providing a compound or compounds which alone or together buffer pH of a liquid composition containing anti-bacterial agent thereby enhancing (i.e., potentiating) the effect of the antibacterial agent even in compositions with very mild surfactant systems.

Fatty acids and their ester derivatives have been used to provide antimicrobial effectiveness in foods, pharmaceuticals and cosmetics (see, for example EP 0,244,144; U.S. Pat. No. 4,002,775; U.S. Pat. No. 4,406,884; U.S. Pat. No. 4,997,851 and Kabara in JAOCS, vol. 61, No. 2, (February, 1984)).

The use of short chain fatty acids generally as potentiators of germicides is also known. These fatty acids, for example, have been used as potentiators with halogenated germicides at high pH and with isethiazolones (see FR 2,223,049 and EP 488,606).

U.S. Pat. No. 3,218,260 to Lewandowski discloses cleaner compositions containing various organic or inorganic acids. The pH of these compositions (less than 2) is well below the pH of the skin cleansing compositions of the present invention.

In none of these references is it taught or suggested that one or more compounds be used either to enhance antibacterial effect in liquid skin cleansing compositions or to potentiate antibacterial compounds which may already be present in liquid skin cleansing compositions at the pH specified by the claims of the subject invention.

Further, none of these references relate to use of hydroxy carboxylic acid (e.g., lactic acid).

U.S. Pat. No. 5,132,037 to Greene et al. teaches aqueous compositions in which $C_8$–$C_{22}$ free fatty acids may be used. All examples (palmitic, stearic) are clearly directed to longer chain fatty acids and there is absolutely no recognition of the antibacterial or potentiating effect of lower chain fatty acids. Also, there is no teaching or suggestion of hydroxy carboxylic acids.

U.S. Pat. No. 5,137,715 to Hoshowski et al. teaches shampoo conditioner compositions wherein the pH of the composition can be in the range of 2.5 to 7.0. The invention requires a polymeric amidoamine compound (substantive compound which imparts conditioning and does not adversely affect foam of anionic; see column 11, line 63 to column 12, line 36). It is further taught that an acid is required to neutralize the amidoamine and one acid which is said to be used for this purpose is citric acid (see column 13, lines 49–65).

The compositions of Hoshowski, while stable, were only stable when using the specific amidoamine of formula I (Example 13 of the patent notes that an extremely similar amidoamine, represented by Formula V, caused instability at pH below 6.0) and, according to examples, 2% citric acid was used.

In general Hoshowski et al. makes clear that most amidoamines would cause instability. More specifically, applicants tried the amidoamine of Formula I in compositions of the subject invention and also found instability. Applicants are not certain whether this instability was due to large amounts of hydroxy acid (applicants use minimum 0.5% lactic acid versus 0.2% citric acid exemplified); whether it was due to the specific hydroxy acid used; or whether it was due to the specific surfactant system. What is clear, however, is that there is no such instability in the system of the invention without the amidoamine of Formula I while there is such instability using the amidoamine in the same system.

U.S. Pat. No. 5,002,680 to Schmidt et al. teach skin cleansing aerosol mousse emulsions comprising:

(A) 88% to 97% of a concentrate comprising:
  (1) 3%–20% anionic or amphoteric;
  (2) 0.05 to 5% polymeric skin feel aid;

(3) 10% to 60% moisturizers (which can be lactic acid); and (4) water; and (B) 3% to 12% propellant.

This reference differs from the subject compositions in a number of ways. First the lactic acid, if used, is used as moisturizing component and must comprise 10% or greater of composition whereas upper level of the hydroxy carboxylic acid of invention (to provide bactericidal effect) is about 9%. Further, the reference is not a single phase composition but comprises propellant (to form mousse). While not wishing to be bound by theory, bactericidal effect of hydroxy acid of invention are believed to be due largely to single phase systems of invention. In a multiphase, it is believed surfactant would not have time to solubilize and enter liquid phase and therefore could not deliver antibacterial activity.

In short, applicants have now found that one or more hydroxy compounds may be used to buffer low pH within a defined low pH range and to therefore:

(1) enhance the antibacterial effect of liquid skin cleansing compositions; and/or (2) potentiate antimicrobial effect of liquid skin cleansing compositions which already contain an antimicrobial agent.

The single phase compositions of the invention are free of amidoamines generally and more specifically, of the amidoamines described in U.S. Pat. No. 5,137,715 to Hoshowski.

BRIEF SUMMARY OF THE INVENTION

The present invention relates to liquid skin cleansing compositions comprising:

(1) any mild surfactant system (i.e., any one or more surfactants which alone or together are demonstrated by clinical tests to be milder than soap itself) in an amount of from about 1–99% by wt., preferably 2–85% by wt., more preferably 3–40% by wt. surfactant system;

(2) 0.5 to about 9%, preferably 0.5 to 5% by weight of a hydroxy carboxylic compound or compounds (e.g., lactic acid) which alone or together buffer the pH of the liquid skin cleanser composition such that the pH is no higher than 5.5 under in-use conditions (i.e., 1:0.5 to 1:100 dilution, preferably 1:1 to 1:25 dilution of product in $H_2O$); and (3) 1% to 99% by wt., preferably 15 to 97%, most preferably 60 to 97% by wt. water.

More specifically, the composition may comprise:

(1) 1% to 99% by wt. of surfactant system comprising:
  (a) 1 to 30% by wt. of at least one anionic surfactant;
  (b) 0.5% to 15% amphoteric surfactant;

(2) 0.5 to 9% hydroxy acid; and (3) 1% to 99% water.

In a second embodiment of the invention, the liquid skin cleansing composition comprises 0.0001% to 5% by weight of an antibacterial agent and the buffering compound or compounds act to potentiate the antimicrobial effect of the composition.

Figure 1:
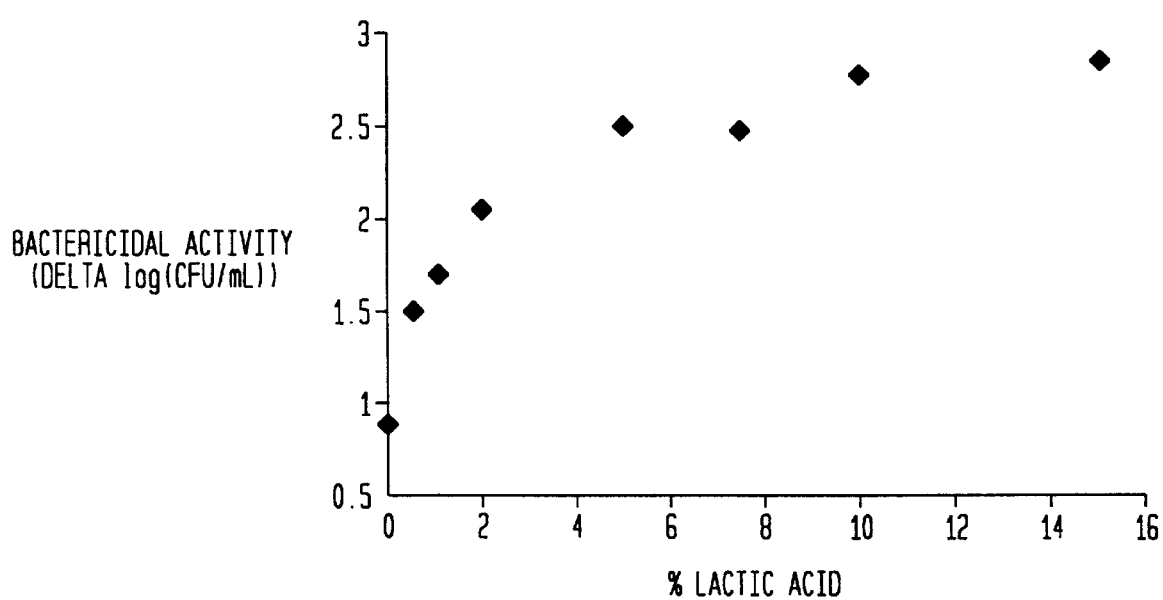
FIG. 1 shows the effect of lactic acid concentration on the bactericidal activity of liquid skin cleansing formulation of the invention which contains an antibacterial agent (e.g., Triclosan or DP300®). As seen, bactericidal activity of the formulation increases with lactic acid content up to about 9%. At 10% and above, bactericidal activity does not increase with increasing lactic acid content.

As shown by Example 3, the particular antibacterial agent selected should have no bearing on the lactic acid effect (i.e., low pH induced by lactic acid is what is causing effect although it should be noted that effect of Triclocarban was superior even to effect of pH alone).

DETAILED DESCRIPTION OF THE INVENTION

The present invention relates to liquid skin cleansing compositions comprising 1 to 99% by weight, preferably 2 to 85%, more preferably 3 to 40% of a mild surfactant system comprising one or more surfactants which alone or together have been clinically tested to be milder than soap itself as measured by zein solubilization test (soap yields 80% zein solubilized). Preferably, the mildness is such that zein solubilization is in the range 10–60% solubilization.

A number of anionic, nonionic, cationic and amphoteric surfactants may be employed in the surfactant system of the invention provided of course that the surfactant, if used alone, or surfactant mixture is milder than would be soap itself as measured by the zein solubilization test.

Among suitable anionic co-actives are the alkyl ether sulfates, acyl isethionates, alkyl ether sulfonates, sarcosinates, sulfosuccinates, taurates and combinations thereof. Among suitable amphoteric co-actives may be included alkylbetaines, amidopropyl betaines, amidopropyl sultaines and combinations thereof.

Alkyl ether sulfates of the present invention will be of the general formula $R-(OCH_2CH_2)_n OSO_3-M^+$ wherein R ranges from $C_8-C_{20}$ alkyl, preferably $C_{12}-C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
| --- | --- | --- | --- |
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standapol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}-C_{15}$ Pareth-15 sulfonate.

Another co-active type suitable for use in the present invention is that of the sulfosuccinates. This category is best represented by the monoalkyl sulfosuccinates having the formula $RO_2CCH_2CH(SO_3-Na^+)COO-M^+$; and amido-MEA sulfosuccinates of the formula $RCONHCH_2CH_2O_2CCH_2CH(SO_3M^+)COO-M^+$; wherein R ranges from $C_8-C_{20}$ alkyl, preferably $C_{12}-C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2$—$M^+$, wherein R ranges from $C_8$–$C_{20}$ alkyl, preferably $C_{12}$–$C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/Sarcosinate | Liquid | W. R. Grace |

Taurates may also be employed in the present invention as co-actives. These materials are generally identified by the formula $RN^+(CH_3)_2CH_2CO_2M^+$, wherein R ranges from $C_8$–$C_{20}$ alkyl, preferably $C_{12}$–$C_{15}$ alkyl, $R^1$ ranges from $C_1$–$C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurates | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CO_2$–$M^+$, amidopropyl betaines of the formula $RCONHCH_2CH_2CH_2N^+(CH_2)_2CH_2CO2$—$M^+$, and amidopropyl sultaines of the formula $RCONHCH_2CH_2N^+(CH_3)_2CH_2SO_3$—$M^+$ wherein R ranges from $C_8$–$C_{20}$ alkyl, preferably $C_{12}$–$C_{15}$ alkyl, and $M^+$ is a sodium potassium, ammonium or triethanolammonium cation. Typical commercial products representative of these co-actives are found in the Table below:

| Trademark | Chemical Name | Physical Form | Manufacturer |
|---|---|---|---|
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula:

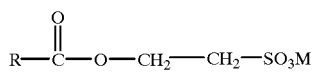

in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application.

Soaps can be used at levels of about 1–10%. Soaps can be used at higher level provided that the surfactant mixture is milder than soap. The soaps may be added neat or made in situ via adding a base, e.g., NaOH; to convert free fatty acids.

Of course, as noted above, soaps should only be used as cosurfactants to the extent that the surfactant system is milder than soap alone.

Surfactant may comprise 1% to 30% by wt. of at least one anionic and 0.5% to 15% amphoteric.

A preferred surfactant active system is one such that acyl isethionate comprises 1 to 15% by weight of the total composition, an anionic other than acyl isethionate (e.g., ammonium lauryl ether sulfate) comprises 1 to 15% by weight of the total composition and amphoteric comprises 0.5 to 15% by weight of the total composition.

BUFFERING COMPONENT

The second critical component of the liquid compositions of the invention is the compound or compounds which alone or together buffer the pH of the formulation under in-use condition such that the pH is from about 2.5 to 5.5, preferably 3.0 to 5.0, more preferably 3.5 to 5.0.

By in-use is meant dilution of 1:0.5 to 1:100, preferably 1:1 to 1:25 of the product in water during use.

This compound or compounds is a hydroxy carboxylic acid which lowers pH of the compositions in use to 2.5 to 5.5 and buffers at this pH.

The hydroxy carboxylic acids include any organic compound having at least one carboxylic acid group and at least one hydroxyl group. Preferably, the chain length of the acid should be $C_2$ to $C_{18}$, more preferably $C_2$ to $C_{12}$. Among the many acids which may be used include citric acid, lactic acid, glycolic acid, α-hydroxy $C_8$ acid, α-hydroxy $C_{16}$ acid, acylated citric acid and β-hydroxybutyric acid. A preferred acid is lactic acid.

In a second embodiment of the invention, the liquid skin cleansing compositions of the subject invention must contain an antibacterial agent. In this embodiment of the invention, the buffering component or compounds described above not only may provide antibacterial effect on its own, but also enhances (potentiates) the antibacterial effectiveness of the antibacterial agent.

The antibacterial agent can be present at a level of from about 0.001% to about 5%, typically from about 0.01% to about 2%, and preferably from about 0.01% to about 1.5% by weight of the composition. The level is selected to provide the desired level of antibacterial activity and can be modified as desired. The preferred antibacterial agent is 2-hydroxy-4,2',4'-trichlorodiphenylether (DP300). Other antibacterial agents are set out below. Many antibacterial agents, known to those skilled in the art and disclosed in e.g., U.S. Pat. Nos. 3,835,057 and 4,714,563, both incorporated hereinbefore by reference, may be used.

Antimicrobials

Suitable antibacterial agents which may be used in the subject invention (i.e., in one embodiment of the invention) include:

2-hydroxy-4,2',4'-trichlorodiphenylether (DP300);

2,6-dimethyl-4-hydroxychlorobenzene (PCMX);

3,4,4'-trichlorocarbanilide (TCC);

3-trifluoromethyl-4,4'-dichlorocarbanilide (TFC);

2,2'-dihydroxy-3,3',5,5',6,6'-hexachlorodiphenylmethane;

2,2'-dihydroxy-3,3',5,5'-tetrachlorodiphenylmethane;

2,2'-dihydroxy-3,3',dibromo-5,5'-dichlorodiphenylmethane;

2-hydroxy-4,4'-dichlorodiphenylether;

2-hydroxy-3,5',4-tribromodiphenylether; and 1-hydroxyl-4-methyl-6-(2,4,4-trimethylpentyl)-2(1H)-pyridinone (Octopirox).

Other suitable antimicrobials include:

Benzalkonium chloride;

Benzethonium chloride;

Carbolic acid;

Cloflucarbon (Irgasan CF3;4,4'-dichloro-3-(trifluoromethyl) carbanilide);

Chlorhexidine (CHX; 1,6-di(4'-chlorophenyl-diguanido) hexane);

Cresylic acid;

Hexetidine (5-amino-1,3-bid(2-ethylhexyl)-5-methylhexahydropyrimidine);

Iodophors;

Methylbenzethonium chloride;

Poly(hexamethylene biguanide) hydrochloride (Cosmocil CQ)

Povidone-iodine;

Tetramethylthiuram disulfide (TMTD; Thiram);

Tribrominated salicylanilide.

In addition to a mild surfactant compound or compounds, the pH buffering compound or compounds, water and optionally (or as required in one embodiment), antimicrobial agent, the liquid skin cleansing compositions may contain optionals as described below.

Each of the above components can be incorporated in an aqueous vehicle which may, in addition, include such materials as organic solvents, such as ethanol, thickeners, such as carboxymethylcellulose, magnesium aluminum silicate, hydroxyethylcellulose, methylcellulose or carbopols; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and perlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The following preservatives may also be used in the liquid skin cleansers of the invention:

| LIQUID SKIN CLEANSER PRESERVATIVES | |
|---|---|
| PRESERVATIVE | CHEMICAL NAME |
| Bronopol | 2-Bromo-2-nitropropane-1,3,diol |
| Dowicil 200 | cis Isomer of 1-(3-chloroallyl)-3,5,5-triaza-1-azoniadamantane-chloride OR Quaternium 15 |
| Glycacil | 3-Iodo-2-propynyl butyl carbamate |
| Glydant XL 1000 | DMDM Hydantoin OR dimethyloldimethylhydantoin |
| Glydant Plus | DMDM Hydantoin and 3-iodo-2-propynyl butyl carbamate |
| Formaldehyde | Formaldehyde |
| Germall 11 | N-(Hydroxymethyl)-N-(1,3-dihydroxymethyl-2,5-dioxo-4-imidazolidinyl)-N'-(hydroxymethyl) urea OR Diazolidinyl urea |
| Germall 115 | N,N'-methylene-bis-[N'-1-(hydroxymethyl)-2,,5-dioxo-4-imidazolidinyl]urea OR imidazolidinyl urea |
| Glutaraldehyde | Glutaraldehyde |
| Kathano CG | Mixture of 5-chloro-2-methyl-4-isothiazoline-3-one- and 2-methyl-4-isothiazoline-3-one OR Mixture of methyl, chloromethyl isothiazolinone, and methyl isothiazolinone |
| Parabens | Methyl Paraben, and Ethyl Paraben, and Propyl Paraben and Buryl Paraben OR those esters of p-hydroxybenzoic acid |
| Phenoxyethanol | 2-Phenoxyethanol |
| Salicylic Acid | Salicylic Acid QR o-Hydroxybenzoic acid |
| Sorbic Acid | Sorbic Acid, Potassium Sorbate |

Coconut acyl mono- or diethanol amides as suds boosters, and strongly ionizing salts such as sodium chloride and sodium sulfate may be used to advantage.

Antioxidants such as, for example butylated hydroxytoluene (BHT) may be used advantageously in amounts of about 0.01% or higher if appropriate.

Cationic conditioners which may be used include Quatrisoft LM-200 (Polyquaternium-24); polyethylene glycols such as

| | | |
|---|---|---|
| Polyox | WSR-205 | PEG 14M, |
| | WSR-N-60K | PEG 45M, or |
| | WSR-N-750 | PEG 7M; and |
| Merquat Plus 3330 - Polyquaternium 39. | | |

Thickeners which may be used include Americoll Polymer HM 1500 (Nonoxynyl Hydroethyl Cellulose); Glucan DOE 120 (PEG 120 Methyl Glucose Dioleate).

Unless stated otherwise, the percentages in the specification, examples and claims are percentages by weight.

Except in the operating and comparative examples, or where otherwise explicitly indicated, all numbers in this description indicating amounts of material (or conditions of reaction and/or use) are to be understood as modified by the word "about".

The following examples are intended for illustrative purposes only and should not be construed to limit the invention in any way.

EXAMPLES

An In vitro Bactericidal Kill Test is used to measure antimicrobial activity in the examples which follow. Methodology for the test is set forth below:

IN VITRO BACTERICIDAL KILL TEST

An in vitro bactericidal test was used to determine the antibacterial effect of products on *Staphylococcus aureus* ATCC #6538 during a short contact time. One milliliter (about $10^8$ cells) of bacteria was exposed for one minute to a one-percent solution of liquid skin cleansing composition. The sample was added to additional water, mixed, and further diluted in 0.1% peptone. Duplicate samples of appropriate dilutions were plated on neutralizing media. In addition, the bacterial culture was plated to determine the actual number of organisms inoculated. the plates were incubated at 34° C. for 48 hours and enumerated. The CFU/ml (colony forming units per milliliter) from dilutions with plate counts in the range of 30–300 were averaged together to produce the final CFU/ml.

The results may be expressed as the log of the CFU/ml. The culture control indicates the actual number of bacteria inoculated while the water control reflects the number of organisms recovered in the absence of product. The lower the number, the more effective the solution was in killing the bacteria.

In this assay, a sampling error of approximately 0.5 log is likely, therefore differences of 0.5 log between products may not be significant. As a result, the data should be viewed in terms of trends rather than as absolute numbers.

Example 1

Applicants carried out an experiment showing that lactic acid concentration on the bacteriocidal activity of liquid skin cleansing formulation. As seen in FIG. 1, the bacteriocidal activity of the formulation increases with lactic acid content up to about 9%. At 10% and above, bactericidal activity does not increase with increasing lactic acid content.

| INGREDIENT | % BY WEIGHT |
|---|---|
| Anionic (Acyl Isethionate) | 1 to 15% |
| Anionic Other than Acyl Isethionate (e.g., SLES)* | 1 to 15% |
| Amphoteric Surfactant** | 5 to 15% |
| pH Buffering (Lactic Acid) | 1 to 5% |

-continued

| INGREDIENT | % BY WEIGHT |
|---|---|
| Sequestrant (EDTA or EHDP) | 0.01 to 0.1% |
| Moisturizer (e.g., Cationic Polymer) | 0.05 to 3.0% |
| Additives (e.g., Dyes, Perfumes) | 0 to 10% |
| Water | Balance |

*SLES - sodium lauryl ether sulfate
**Cocoamidopropyl betaine

Example 2

The compound or compounds of the invention may also be used in the following formulations.

| COMPONENT | % BY WEIGHT |
|---|---|
| FORMULATION 1 | |
| Sodium Isethionate | 3–5% |
| Sodium Alkene Benzene Sulfonate | 1–3% |
| Sodium Laureth Sulfate | 3–5% |
| Sodium Cocoyl Isethionate | 8–12% |
| Sodium Tallow/Coconut Soap | 1–3% |
| Preservative (e.g., Methylparaben) | .1–.5% |
| Sequestrants | .01–.05% |
| Fatty Acid (e.g., Stearic Acid) | 7–10% |
| Sulfosuccinate | 3–5% |
| Water plus minors | to balance |
| FORMULATION 2 | |
| Sodium Cocoyl Isethionate | 5–8% |
| Cocamidopropyl Betaine | 5–8% |
| Sulfosuccinate | 2–5% |
| Fatty Acid | 6–9% |
| Sodium Isethionate | 1–3% |
| Silicone Emulsion | 3–7% |
| Sequestrant | .01–.05% |
| Water plus minors | to balance |

Example 3

Applicants sought to show that the antibacterial effect provided by low pH compositions comprising lactic acid is not dependent on the specific antibacterial compound selected. In this regard, applicants prepared compositions as noted below:

| CONTROL | |
|---|---|
| COMPONENT | % BY WEIGHT |
| Sodium Cocoyl Isethionate | 6–8% |
| Sodium Laureth Sulfate | 5–7% |
| Cocamidopropyl Betaine | 1–3% |
| Cationic Polymer | 0.1% |
| EDTA | 0.01–0.03% |
| Antibacterial | 0.25% |
| Lactic Acid | 0.1–5.0%* |
| Water | To balance |

*Range varied according to pH. Approximately 0.1% was actually used in the experiments conducted.

Using the bacteriocidal kill test described above, various antibacterial compounds were used and results set forth below:

| Organism | Sample | pH (Undiluted) | CFU/ml | Log$_{10}$ CFU/ml |
|---|---|---|---|---|
| S. aureus ATC 6538 | S. aureus Control Count | — | 3.80 × 10$^8$ | 8.58 |
| | Water | — | 2.62 × 10$^8$ | 8.42 |
| | Control (Composition alone) | 4.00 | 6.20 × 10$^7$ | 7.79 |
| | | 4.54 | 1.47 × 10$^8$ | 8.17 |
| | | 4.88 | 1.59 × 10$^8$ | 8.20 |
| | Control + 0.25% Cosmocil CQ[1/] | 4.00 | 5.70 × 10$^7$ | 7.76 |
| | | 4.50 | 1.54 × 10$^8$ | 8.19 |
| | | 4.96 | 1.65 × 10$^8$ | 8.22 |
| | Control + 0.25% PCMX[2/] | 4.02 | 3.50 × 10$^7$ | 7.54 |
| | | 4.50 | 1.48 × 10$^8$ | 8.17 |
| | | 4.97 | 1.47 × 10$^8$ | 8.17 |
| | Control + 0.25% Triclosan (DP300)[3/] | 4.01 | 4.60 × 10$^7$ | 7.66 |
| | | 4.48 | 1.05 × 10$^8$ | 8.02 |
| | | 5.01 | 1.46 × 10$^8$ | 8.16 |
| | Control + 0.25% Triclocarban (TCC)[4/] | 3.97 | 7.00 × 10$^6$ | 6.85 |
| | | 4.54 | 3.90 × 10$^7$ | 7.59 |
| | | 4.97 | 4.60 × 10$^7$ | 7.66 |
| | Control + 0.25% Benzalkonium Chloride | 3.88 | 8.50 × 10$^7$ | 7.93 |
| | | 4.56 | 1.82 × 10$^8$ | 8.26 |
| | | 4.80 | 1.88 × 10$^8$ | 8.27 |
| | Control + 0.25% Chlorhexidine | 4.04 | 8.60 × 10$^7$ | 7.93 |
| | | 4.49 | 1.45 × 10$^8$ | 8.16 |
| | | 4.97 | 2.02 × 10$^8$ | 8.31 |

[1/]Poly(hexamethylene biguanide)hydrochloride
[2/]2,6-dimethyl-4-hydrochlorobenzene
[3/]2-hydroxy-4,2',4'-trichlorodiphenylether
[4/]3,4,4'-trichlorocarbanilide As can be seen from the results, it was low pH (i.e., using lactic acid buffer) which provided enhanced antibacterial effect relative to water regardless of which antibacterial agent was used (except in case of Triclorcarban where antibacterial effect was superior even to pH effect). This clearly shows that the enhanced bactericidal activity of lactic acid (as observed in FIG. 1) is independent of antibacterial agent chosen.

Example 4

In a separate experiment, applicants prepared the following formulation containing NaOH and slightly more lactic acid to both the compositions.

| CONTROL | |
|---|---|
| COMPONENT | % BY WEIGHT |
| Sodium Laureth Sulfate | 4–5% |
| Sodium Olefin Sulfonate | 2–3% |
| Cocamidopropyl Betaine | 2–4% |
| Cationic Polymer | 2% |
| Ethylene Glycol Monostearate | 1% |
| NaOH | ~40% |
| Lactic Acid | ~2% |
| Perfume, Preservatives & Water | To Balance |

Again, using the bacteriocidal test described above, various antibacterial compounds were used and results set forth below.

| BASIN INOCULATION TEST (BIS 102798) | | | | |
|---|---|---|---|---|
| Organism | Sample | pH (Undiluted) | CFU/ml | Log$_{10}$ CFU/ml |
| S. aureus ATCC 6538 | S. aureus Control Count | — | 2.55 × 10$^8$ | 8.41 |
| | Water | — | 2.38 × 10$^6$ | 8.38 |
| | Control | 4.0 | 1.21 × 10$^6$ | 6.08 |
| | | 4:5 | 1.36 × 10$^6$ | 6.13 |
| | | 5.5 | 1.20 × 10$^7$ | 7.08 |
| | Control + 0.25% Cosmocil CQ | 4.0 | 6.5 × 10$^5$ | 5.81 |
| | | 4.5 | 1.24 × 10$^6$ | 6.09 |
| | | 5.5 | 1.55 × 10$^7$ | 7.19 |
| | Control + 0.25% PCMX | 4.4 | 1.69 × 10$^5$ | 5.23 |
| | | 4.5 | 1.04 × 10$^6$ | 6.02 |
| | | 5.5 | 1.21 × 10$^7$ | 7.08 |
| | Control + 0.25% | 4.0 | 5.10 × 10$^5$ | 5.71 |
| | | 4.5 | 1.75 × 10$^6$ | 6.24 |
| | Triclosan Control + 0.25% | 5.5 | 1.15 × 10$^7$ | 7.06 |
| | | 4.0 | 7.10 × 10$^5$ | 5.85 |
| | | 4.5 | 1.24 × 10$^6$ | 6.09 |
| | Triclocarban Control + 0.25% | 5.5 | 1.96 × 10$^7$ | 7.29 |
| | | 4.0 | 4.00 × 10$^5$ | 5.60 |
| | Benzalkonium Chloride | 4.5 | 7.10 × 10$^5$ | 5.85 |
| | | 5.5 | 1.10 × 10$^7$ | 7.04 |
| | Control + 0.25% | 4.0 | 6.50 × 10$^5$ | 5.81 |
| | | 4.5 | 1.31 × 10$^6$ | 6.12 |
| | Chlorhexidine | 5.5 | 4.90 × 10$^7$ | 7.69 |

Control was used as the base

We claim:

1. A skin cleansing composition comprising:

(1) 1% to 15% by weight acyl isethionate;

(2) 1% to 15% by weight of an an ionic surfactant other than acyl isethionate;

(3) 5% to 15% by weight of an amphoteric surfactant;

(4) 0.5% to 9% by weight lactic acid;

(5) 0.001% to 5% by weight of an antibacterial agent wherein said antibacterial agent is selected from the group consisting of:
2,6-dimethyl-4-hydroxychlorobenzene;
3,4,4'-trichlorocarbanilide;
Benzalkonium chloride;
Chlorhexidine;
Poly(hexamethylene biguanide) hydrochloride and mixtures thereof; and (6) balance water, wherein pH is from about 2.5 to less than 5.0.

2. A composition according to claim 1, wherein pH is from about 3.0 to less than 5.0.

* * * * *